United States Patent

Friedrich et al.

(10) Patent No.: US 10,081,831 B2
(45) Date of Patent: Sep. 25, 2018

(54) METHOD AND ARRANGEMENT FOR CALIBRATING A SENSOR ELEMENT

(75) Inventors: Katja Friedrich, Nürnberg (DE);
Walter Gumbrecht, Herzogenaurach (DE); Peter Paulicka, Erlangen (DE);
Manfred Stanzel, Erlangen (DE);
Renee Weber, Langenau-Albeck (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 672 days.

(21) Appl. No.: 12/743,316

(22) PCT Filed: Oct. 29, 2008

(86) PCT No.: PCT/EP2008/064680
§ 371 (c)(1),
(2), (4) Date: May 17, 2010

(87) PCT Pub. No.: WO2009/065711
PCT Pub. Date: May 28, 2009

(65) Prior Publication Data
US 2010/0248243 A1 Sep. 30, 2010

(30) Foreign Application Priority Data
Nov. 20, 2007 (DE) .................. 10 2007 055 386

(51) Int. Cl.
*C12Q 1/68* (2018.01)
*C12Q 1/6837* (2018.01)

(52) U.S. Cl.
CPC .................................. *C12Q 1/6837* (2013.01)

(58) Field of Classification Search
None
See application file for complete search history.

(56) References Cited

U.S. PATENT DOCUMENTS 5,599,668 A * 2/1997 Stimpson ............. C12Q 1/6825
435/5
5,843,667 A * 12/1998 Weisburg ............. C12Q 1/689
435/6.12

(Continued)

FOREIGN PATENT DOCUMENTS

DE   10025384 A1   2/2002
DE   10126341 A1   12/2002

(Continued)

OTHER PUBLICATIONS

Kummerlen et al, Mol. Phys., vol. 80, pp. 1031-1046 (1993). (Year: 1993).*

(Continued)

*Primary Examiner* — Robert T. Crow
(74) *Attorney, Agent, or Firm* — David S. Safran

(57) ABSTRACT

A method is disclosed for calibrating a sensor element, which has an immobilized probe oligonucleotide, via which the bonding of a target nucleic acid (Z) can be detected by the sensor. In at least one embodiment, the method includes: a) bringing the sensor element into contact with a control nucleic acid (K), the melting temperature Tm(K) of which is less than the melting temperature Tm(Z) of the target nucleic acid (Z); b) hybridizing the control nucleic acid (K) to the probe oligonucleotide at a temperature T[p]<Tm(K), and detecting a positive control signal; and optionally c) modifying the stringent conditions such that T[n]>Tm(K) and detecting a negative control signal at a temperature T[n]. According to a refinement of at least one embodiment of the invention, a measuring signal of the target nucleic acid (Z) is measured at a measuring temperature T [mess], where Tm(K)<T[mess]<Tm(Z). The method is suited in particular for the calibration and quality control of microarrays.

13 Claims, 5 Drawing Sheets

(56) References Cited

U.S. PATENT DOCUMENTS

| | | | | |
|---|---|---|---|---|
| 6,132,971 A | * | 10/2000 | Thorp | B82Y 15/00 435/6.13 |
| 6,346,383 B1 | | 2/2002 | Kajiyama et al. | |
| 6,471,916 B1 | * | 10/2002 | Noblett | C12Q 1/6837 250/252.1 |
| 6,545,758 B1 | | 2/2003 | Sandstrom | |
| 6,673,536 B1 | | 1/2004 | Stoughton et al. | |
| 7,225,082 B1 | * | 5/2007 | Natan | B01J 13/0047 257/40 |
| 2001/0014446 A1 | * | 8/2001 | Heroux | C12Q 1/6834 435/6.1 |
| 2002/0012940 A1 | | 1/2002 | Lockhart et al. | 435/6 |
| 2002/0022226 A1 | | 2/2002 | Nakao et al. | |
| 2002/0125136 A1 | * | 9/2002 | Sharaf | G01N 27/44726 204/461 |
| 2003/0077839 A1 | * | 4/2003 | Takei | G01N 33/54313 436/177 |
| 2003/0143581 A1 | * | 7/2003 | Franzen | B82Y 5/00 435/6.11 |
| 2003/0186310 A1 | * | 10/2003 | Kincaid | B01J 19/0046 435/6.11 |
| 2003/0203394 A1 | * | 10/2003 | Eichen | C12Q 1/6816 435/6.18 |
| 2004/0052729 A1 | * | 3/2004 | Penades | A61K 9/5115 424/1.73 |
| 2004/0081974 A1 | | 4/2004 | Gao | |
| 2004/0091870 A1 | * | 5/2004 | Pabich | C07H 21/04 435/6.15 |
| 2004/0101835 A1 | * | 5/2004 | Willis | C12Q 1/6827 435/6.12 |
| 2004/0132080 A1 | | 7/2004 | Kawaguchi et al. | |
| 2005/0048485 A1 | * | 3/2005 | Kurane et al. | 435/6 |
| 2005/0074787 A1 | * | 4/2005 | Fan et al. | 435/6 |
| 2006/0040378 A1 | * | 2/2006 | Arinaga | G01N 33/5438 435/287.2 |
| 2006/0105354 A1 | * | 5/2006 | Remacle et al. | 435/6 |
| 2006/0115851 A1 | | 6/2006 | Samartzidou et al. | |
| 2006/0228703 A1 | | 10/2006 | Hartwich et al. | |
| 2007/0003958 A1 | | 1/2007 | Okamoto et al. | |
| 2007/0037153 A1 | * | 2/2007 | Mandrand | B82Y 5/00 435/6.12 |
| 2007/0092869 A1 | | 4/2007 | Fulmer-Smentek et al. | |
| 2007/0207456 A1 | * | 9/2007 | Pourmand | C12Q 1/708 435/5 |
| 2007/0264630 A1 | | 11/2007 | Gumbrecht et al. | |
| 2010/0248243 A1 | * | 9/2010 | Friedrich | C12Q 1/6837 435/287.2 |

FOREIGN PATENT DOCUMENTS

| | | | |
|---|---|---|---|
| DE | 10141691 A1 | 3/2003 | |
| DE | 10324912 A1 | 1/2005 | |
| EP | 1108472 A2 | 6/2001 | |
| EP | 1132485 A2 | 9/2001 | |
| EP | 1186673 A2 | 3/2002 | |
| JP | 2003329676 A | * 11/2001 | G01N 33/53 |
| WO | WO 0123600 A2 | 4/2001 | |
| WO | WO 0214838 A2 | 2/2002 | |
| WO | WO 02097413 A2 | 12/2002 | |
| WO | WO 2004106546 A1 | 12/2004 | |
| WO | WO 2005064012 A2 | 7/2005 | |
| WO | WO 2007062666 A1 | 6/2007 | |

OTHER PUBLICATIONS

Office Action for German patent application No. 08 852 553.0 dated Feb. 24, 2011.

* cited by examiner

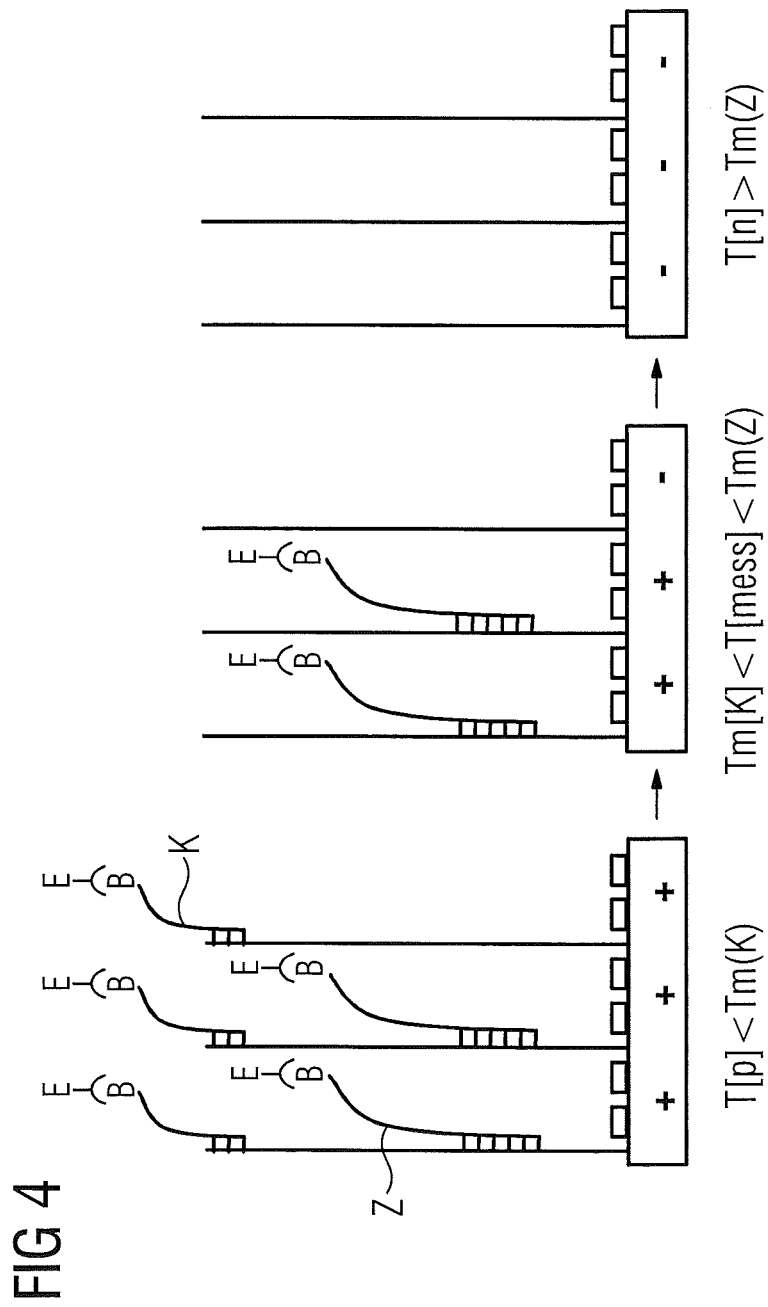

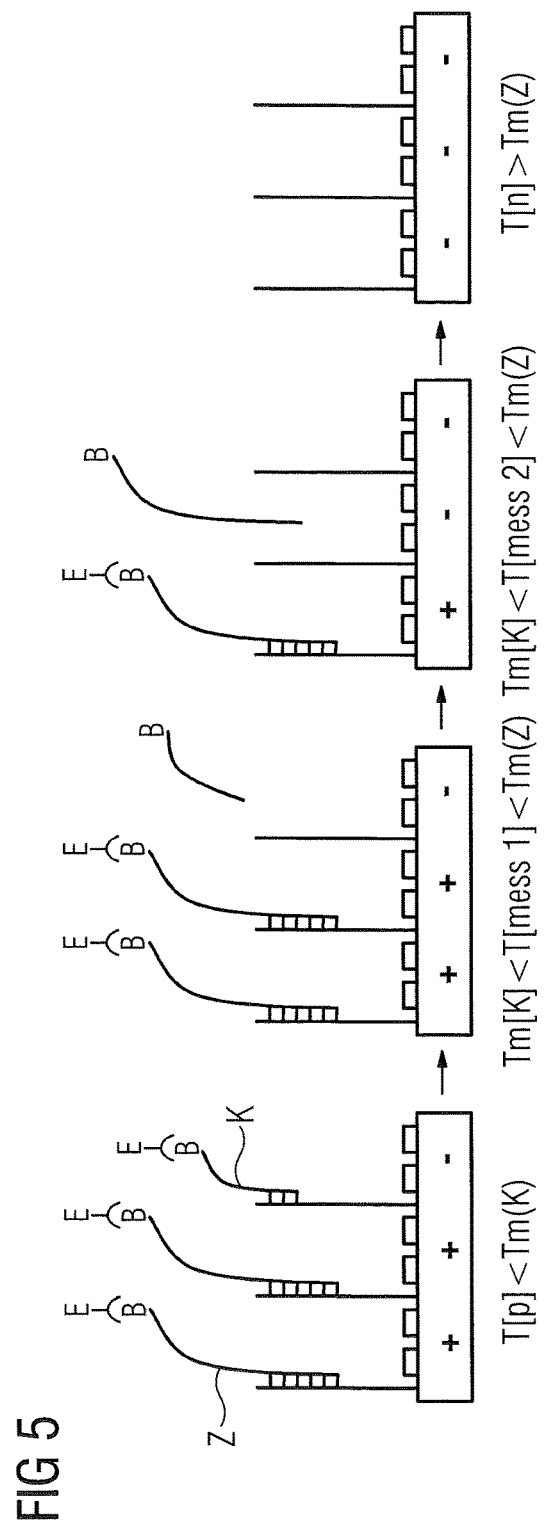

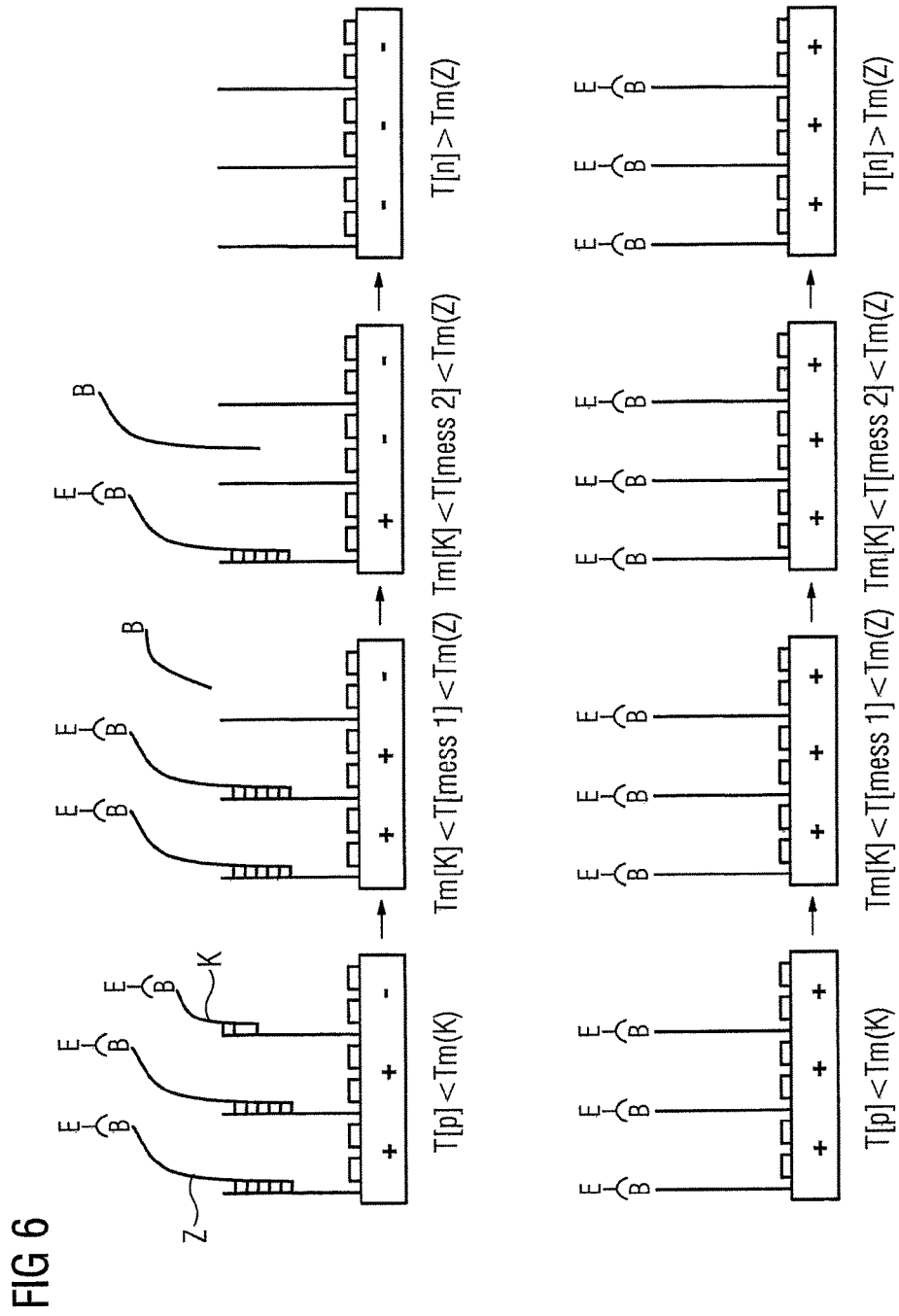

METHOD AND ARRANGEMENT FOR CALIBRATING A SENSOR ELEMENT

PRIORITY STATEMENT

This application is the national phase under 35 U.S.C. § 371 of PCT International Application No. PCT/EP2008/064680 which has an International filing date of Oct. 29, 2008, which designates the United States of America, and which claims priority on German patent application number DE 10 2007 055 386.4 filed Nov. 20, 2007, the entire contents of each of which are hereby incorporated herein by reference.

FIELD

At least one embodiment of the invention generally relates to a method and/or to an arrangement for calibrating sensor elements, more specifically for calibrating sensor elements on microarray arrangements.

BACKGROUND

The development of microarray-based methods in nucleic acid analysis has made rapid progress in recent years. A microarray arrangement is an arrangement of a matrix of probe molecules attached to a sensor in individual, addressable positions in such a way that each position in the array arrangement forms a sensor element by which a target molecule can be detected. The probe molecules used in nucleic acid analysis are usually probe oligonucleotides which have been immobilized ("spotted") e.g. in an arrangement in the form of a chip in a screen-like matrix on a support. Hybridization with a complementary target nucleic acid results in binding to the probe oligonucleotide. This binding may then be detected by a plurality of alternative methods such that the presence of the target nucleic acid (Z) can be recorded and optionally also quantified owing to the binding event. The detection principle employed may be optical, electrochemical, gravimetric, magnetic and other suitable methods.

Optical methods involve the target nucleic acid or the hybrid of probe oligonucleotide and target nucleic acid being labeled by a label which results in an optically detectable signal. Said label may be a dye, a fluorophore, a chromophore, an intercalating dye, a fluorescent dye or the like. When a binding event occurs, an optically detectable signal can be recorded, for example by a CCD camera capable of taking an image of the entire array, at the addressable position of the particular probe oligonucleotide.

Electrochemical detection methods may involve the probe oligonucleotides being immobilized on an electrochemical sensor. The target nucleic acid or the hybrid of probe oligonucleotide and target nucleic acid is labeled by a label which modifies the electrochemical properties on the sensor element locally at the position of the particular probe oligonucleotide, thus enabling an electric signal, for example a voltage, a current, a change in capacity or the like to be measured. A corresponding method has been disclosed in DE 101 341. This method comprises labeling target nucleic acids with biotin, labeling, after hybridization of the target nucleic acid to the probe oligonucleotide, the bound target nucleic acid with streptavidin-alkaline phosphatase, and presenting to the alkaline phosphatase an enzyme substrate which, when converted by the phosphatase, results in a product which changes conductivity locally, thus enabling a local increase in current to be measured at the electrode on which the probe oligonucleotide has been immobilized.

Gravimetric methods involve recording a signal which results from the change in mass upon hybridization of the target nucleic acid to the probe oligonucleotide. Examples of known methods are "FBAR" and "cantilever" methods.

Magnetic detection involves the probe oligonucleotide being immobilized on a magnetic sensor element, for example a GMR sensor. The target nucleic acid or the hybrid of probe oligonucleotide and target nucleic acid may then be labeled, for example, with paramagnetic particles, for example iron oxide nanoparticles, thus enabling a change in magnetic properties upon binding of the target nucleic acid to be recorded locally at the position of the probe oligonucleotide.

A problem surfacing in all of the detection principles is the fact that qualitative differences between individual sensor elements may appear, which may result in signals of different strengths, especially in the case of highly sensitive and quantitative or semiquantitative measurement methods. Other external influences, for example temperature fluctuations or temperature gradients, flow fluctuations or flow gradients caused by sensor surface fluidics, and other factors, may also result in the fact that not all of the sensor elements in a microarray arrangement have the same sensitivity or, at a correspondingly similar target nucleic acid (Z) concentration, provide a signal having the same strength. Thus, for example, sensor elements on the edge of a microarray arrangement are known to behave differently from sensor elements in the center of a microarray arrangement.

The reliable, error-free operation of assays based on microarrays thus requires a reliable and error-free quality control. The latter must include especially the essential elements of positive and negative control. To this end, a particular sensor element should ideally be calibrated by means of a two-point calibration, i.e. each sensor should be loaded also with two known samples (sample concentrations) in addition to the sample to be determined, with the respective measurement signals being recorded.

This procedure is very difficult to implement, in particular for microarray systems having a high number of sensor elements or addressable positions, since a two-point calibration system usually requires complex and expensive measures. Technology is known to solve or to avoid this problem by designing various sensor element positions in the microarray arrangement as control sensor elements (control spots). The disadvantage here, however, is the necessary assumption that the various sensors behave in an absolutely identical manner, and that the designed control spots are representative of all sensor elements.

SUMMARY

At least one embodiment of the invention provides a simple, inexpensive two-point calibration that can be carried out in each case with one and the same sensor element which is also used as a sensor for a target nucleic acid. At least one embodiment is achieved according to the invention by a method and at least one embodiment is achieved by an arrangement. Advantageous developments of the invention are described in the dependent claims.

At least one embodiment of the invention relates to a method for calibrating a sensor element having an immobilized probe oligonucleotide, via which the sensor can record binding of a target nucleic acid (Z), comprising:

a) contacting the sensor element with a control nucleic acid (K), the melting temperature of which, Tm(K), is lower than the melting temperature of the target nucleic acid, Tm(Z);
b) hybridizing the control nucleic acid (K) to the probe oligonucleotide at a temperature T[p]<Tm(K), and recording a positive control signal; and optionally
c) modifying the stringency conditions such that T[n]>Tm(K), and recording a negative control signal.

At least one embodiment of the invention further relates to a method for calibrating a sensor element, comprising:
a) contacting the sensor element with a mixture having control nucleic acid (K) and target nucleic acid (Z), with the melting temperature of the control nucleic acid, Tm(K), being lower than the melting temperature of the target nucleic acid, Tm(Z);
b1) hybridizing the mixture to the probe oligonucleotide at a temperature T[p]<Tm(K), and recording a positive control signal;
b2) modifying the stringency conditions at T=T[mess] such that: Tm(K)<T[mess]<Tm(Z), and recording a measurement signal; and optionally
c) modifying the stringency conditions such that T[n]>Tm(Z), and recording a negative control signal.

Tm(K) is the melting temperature of the control nucleic acid at given solvent conditions.

Tm(Z) is the melting temperature of the target nucleic acid at given solvent conditions.

T[n] is the temperature at which the negative control signal is measured.

T[p] is the temperature at which the positive control signal is measured.

T[mess] is the temperature at which a measurement signal is measured.

The stringency conditions are preferably modified by increasing the temperature. Alternatively, they may be modified by modifying the solvent conditions or by modifying a combination of solvent conditions and temperature.

According to another aspect of at least one embodiment of the invention, a plurality of measurement signals, 1 to n, may be measured at different temperatures T[mess 1–n], where Tm(K)<T[mess 1–n]<Tm(Z).

According to another aspect of at least one embodiment of the invention, the method may be carried out for a majority of sensor elements arranged in an array arrangement.

According to another aspect of at least one embodiment of the invention, target nucleic acid and control nucleic acid may be labeled with a detectable label.

Target nucleic acid and control nucleic acid may be labeled directly (for example with a dye, enzyme, or the like), but they may also be labeled indirectly (for example with biotin, a recognition sequence for a secondary binding partner with label, or the like).

According to another aspect of at least one embodiment of the invention, the detectable label may be an enzymatic label capable of converting a substrate into a product detectable by the sensor element.

According to another aspect of at least one embodiment of the invention, step (a) may be preceded by contacting the sensor element with detectable product in order to record a first calibration signal.

According to another aspect of at least one embodiment of the invention, additionally a temperature compensation signal may be recorded at each of the temperatures T[p], T[mess], T[mess 1–n] and T[n] on a further sensor element on which detectable label is immobilized directly.

According to another aspect of at least one embodiment of the invention, the sensor element may be an electrochemical sensor element, and target nucleic acid and control nucleic acid may be labeled with a detectable label which is an enzymatic label converting a substrate into a product detectable by the sensor element.

The enzymatic label may particularly be a phosphatase.

According to another aspect of at least one embodiment of the invention, the melting temperature Tm(K) of the control nucleic acid (K) is preferably at least 5° C. lower, more preferably at least 10° C. lower, than the melting temperature Tm(Z) of the target nucleic acid (Z).

According to another aspect of at least one embodiment of the invention, preference may be given to using as control nucleic acid a nucleic acid composition having randomized deca-oligonucleotide sequences. Randomized 6-, 7-, 8-, 9-, 11-, 12-, 13-, 14- or 15-mers may also be used. Particular preference is given to biotinylated oligomers. Likewise possible are control nucleic acids carrying a specific recognition sequence which binds to a specific complementary sequence on the probe oligonucleotide of the sensor element, with said complementary sequence of the probe oligonucleotide not binding to the target nucleic acid.

At least one embodiment of the invention further relates to an arrangement, comprising:
at least one sensor element with a probe nucleotide immobilized thereon, via which the sensor element can record binding of a target nucleic acid (Z), wherein a binding complex of probe oligonucleotide and target nucleic acid has a melting temperature Tm(Z);
heating and/or cooling means for changing the temperature at the sensor element;
at least one control nucleic acid capable of forming with the probe nucleotide a binding complex which has a melting temperature of Tm(K)<Tm(Z).

According to another aspect of at least one embodiment of the invention, the arrangement further comprises a majority of sensor elements arranged in an array arrangement. The sensor elements may be designed by way of a microarray, for example a biochip. The array arrangement may be implemented as part of a microfluidic apparatus. A microfluidic apparatus is an apparatus in which fluids, in particular liquids in volumes in the microliter range, may be processed.

According to another aspect of at least one embodiment of the invention, the control nucleic acid is stored by way of a dry reagent in the arrangement. The control nucleic acid is dissolved by introducing an appropriate solvent (for example a buffer solution) and may then bind to probe oligonucleotides.

According to another aspect of at least one embodiment of the invention, the arrangement is designed by way of a kit comprising an apparatus which comprises the heating and/or cooling means and the at least one sensor element, and comprising a composition having the control nucleic acid.

According to another aspect of at least one embodiment of the invention, the control nucleic acid is labeled with a detectable label.

According to another aspect of at least one embodiment of the invention, the detectable label is an enzymatic label capable of converting a substrate into a product detectable by the sensor element.

According to another aspect of at least one embodiment of the invention, detectable label is immobilized directly on a further sensor element.

According to another aspect of at least one embodiment of the invention, the sensor element of the arrangement is an electrochemical sensor element, and the control nucleic acid is labeled with a detectable label which is an enzymatic label converting a substrate into a product detectable by the sensor element.

According to another aspect of at least one embodiment of the invention, the arrangement comprises as control nucleic acid a nucleic acid composition having randomized deca-oligonucleotide sequences.

According to another aspect of at least one embodiment of the invention, the nucleic acids are biotinylated with randomized deca-oligonucleotide sequences.

For the purpose of at least one embodiment of the present invention, a sensor element is an element capable of recording a signal which can be utilized for measurements upon binding of a target nucleic acid (Z) to a probe oligonucleotide associated with the sensor element. The signal may be a qualitative or a quantitative signal. The signal is preferably quantitative, i.e. the signal strength correlates with the amount of target nucleic acids bound.

A probe oligonucleotide is an oligonucleotide used as a probe for binding a target nucleic acid. Preference is given to the probe oligonucleotide being a single-stranded nucleic acid. The probe nucleotide may be constructed with DNA, RNA or synthetic or modified nucleotide analogs. Preference is given to the probe oligonucleotide having a defined sequence. The probe oligonucleotide is preferably more than 10 nucleotides, more preferably more than 20 nucleotides, in length. An "immobilized" probe oligonucleotide means a nucleotide which is spatially fixed on the sensor element or in sufficient spatial proximity to the sensor element, such that it maintains its position at the sensor element or sufficiently close to the sensor element under the conditions under which measurements are carried out at said probe sensor element.

The probe oligonucleotide may be applied directly to the sensor element, for example on the electrode of an electrochemical sensor element, or in immediate spatial proximity to the sensor element, it may be immobilized indirectly, for example via a spacer molecule, or be immobilized by a compartment, i.e. by a delimitation or encapsulation. A control nucleic acid for the purpose of the present invention is a nucleic acid which can likewise hybridize to the probe oligonucleotide, but with the hybrid of probe oligonucleotide and control nucleic acid (K) having a lower melting temperature than the hybrid of probe oligonucleotide and target nucleic acid (Z). This is usually achieved by the complementary strand, via which control nucleic acid and probe oligonucleotide hybridize, being shorter than the length of the strand via which the target nucleic acid hybridizes with the probe oligonucleotide. This will be discussed in more detail hereinbelow. The term "to hybridize" encompasses the contacting of two nucleic acids (e.g. probe oligonucleotide and control nucleic acid) under conditions (temperature, pH, buffer composition, salt concentration) which enable hybrids to form via complementary strands.

The term "recording a signal" includes all the steps and requirements necessary for enabling a signal to be measured off the sensor element, which can indicate binding of a nucleic acid to the probe oligonucleotide. In the case of direct labeling, labeling of the target nucleic acid with a dye, the signal can be recorded, for example, directly with the aid of a CCD camera. With indirect labeling, for example by biotinylation of the target nucleic acid or control nucleic acid, the term "recording a signal" for the purpose of the present invention shall also include any further steps required (incubation with streptavidin-enzyme complex, washing steps, incubation with enzyme substrate and measuring the measurement signal).

The term positive control signal means for the purpose of the present invention a signal which corresponds, under the conditions (temperature, etc.) given in each case, to the maximum signal strength that can be measured off the sensor element. This is the case, for example, if all the individual probe oligonucleotide molecules have bound a binding partner.

The term negative control signal denotes in the context of the present invention a signal which corresponds to a minimum signal or a background noise for the respective sensor element under the particular measuring conditions. This is the case, for example, if none of the individual probe oligonucleotide molecules has bound a binding partner when the signal is recorded.

An array arrangement means an arrangement of individual sensor elements which are arranged in individually addressable positions.

A detectable label means in the context of the present invention a label by which a measurable signal can be recorded directly or indirectly. This may be a direct label, for example a dye, fluorescent dye, radioactive label, etc. However, the term detectable label also encompasses indirect labeling which requires further steps for recording a measurable signal, for example biotin labeling, antibody labeling, enzyme labeling, etc.

Choosing a sequence and its length in base pairs for a probe oligonucleotide is subject to a multiplicity of considerations. The length of a probe oligonucleotide sequence may not exceed a particular length. The melting temperature of the duplex of probe oligonucleotide and target nucleic acid increases as a function of the length of the probe oligonucleotide. The melting temperature (Tm) is the temperature at which the probe oligonucleotide detaches (melts) from the target nucleic acid, or in other words: it hybridizes with the target nucleic acid below its melting temperature. With constant external conditions (solvent conditions), however, the melting temperature of a double-stranded nucleic acid is a function not only of its length but also of its nucleotide composition. G-C base pairs are stabilized by three hydrogen bonds, T-A base pairs are stabilized only by two hydrogen bonds. G-C base pairs are thus "more stable". The melting temperature thus increases to a greater extent with the number of G nucleotides and C nucleotides. The melting temperature can be calculated by multiple methods, with the information being based in each case on ° C.:

The GC method is a simple but also imprecise method:

$Tm(° C.)=(64+41*(\% GC-16.4))° C.$ where % GC is the proportion of G and C bases of the total number of bases.

The "salt adjusted" method is a little more precise and takes into account the concentration of Na+ ions in the reaction mixture:

$Tm(° C.)=(100.5+41*\% GC-(820:L)*16.6 \log [Na+])° C.$ where L is the total number of bases and [Na+] indicates the concentration of Na+ ions.

Another method is the "base stacking" method which includes the enthalpy and entropy terms of helix formation during hybridization.

Other components of the solvent also influence the melting temperature, in particular if formamide is used for controlling the hybridization conditions. The temperature can be estimated using the following formula and taking into account these parameters:

$Tm = 81.5 + 0.41*(\% \ GC) + 16.6 \log [Na+] - (820:L) - 0.61*(\% \text{ formamide}) - 1.4 (\% \text{ mismatch})$ where % mismatch=proportion of mismatched bases. The hybridization temperature should optimally be about 5-10° C. below the melting temperature for DNA/DNA hybrids, with 5° C. being sufficient in the case of DNA/RNA hybrids.

Different approximation formulae are used for shorter sequences. A proven way of estimating the hybridization temperature in practice is the (4+2) rule involving counting 4° C. for each cytosine and each guanine, and 2° C. for each adenine and each thymidine. This sum minus 5-10° C. gives the approximate hybridization temperature. The various formulae for approximately calculating the melting temperature indicate that aside from the length of the probe (length of the complementary region), GC content, salt concentration and nature of the solvent also determine the melting temperature. These parameters combined are the stringency conditions which decide whether or not two complementary or at least partially complementary nucleic acid strands hybridize. Accordingly, the stringency conditions may be modified and hybridization (also referred to as "annealing") or melting or dissolving of the double strands may be controlled by varying the parameters temperature, salt concentration, solvent composition.

Meanwhile, there is also a large amount of software which can be used for calculating the melting temperature of sequences.

BRIEF DESCRIPTION OF THE DRAWINGS

The invention will now be described by way of illustration and example embodiments on the basis of examples and the appended figures in which:

FIG. 4: is a diagram of another embodiment of the invention;

FIG. 5: is a diagram of another embodiment of the invention; and

FIG. 6: is a diagram of another embodiment of the invention.

DETAILED DESCRIPTION OF THE EXAMPLE EMBODIMENTS

Figure 1:
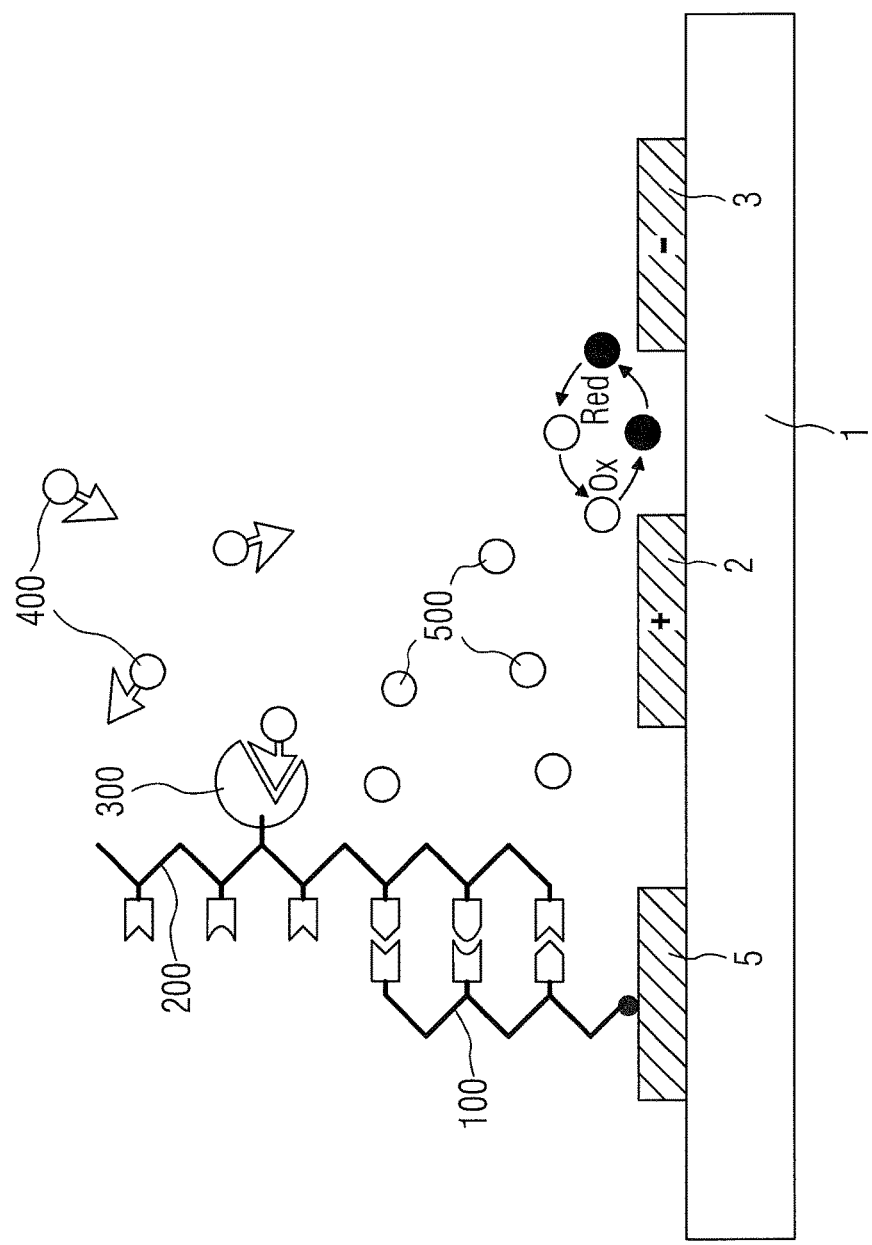
FIG. 1: is a diagram of an example sensor element as used in the method of an embodiment of the invention.

FIG. 1 depicts an example sensor element having a measuring arrangement with two electrodes 2 and 3, with additionally a gold surface 5 being present, on which a probe oligonucleotide 100 has been immobilized. Alternatively, corresponding probe oligonucleotides may also be immobilized directly on the electrodes 2, 3. Corresponding sensor elements are described in detail, for example, in DE 101 26 341 A1.

FIG. 1 depicts diagrammatically a substrate 1 with a planar surface formed, for example, by the crystallographic surface of a silicon chip. An array of electrochemical detectors 2, 3 is designed on the substrate 1 in predefined array positions, which are used for carrying out bioanalytical studies involving enzyme-coupled reactions. In detail, a probe oligonucleotide is denoted 100, an analyte molecule is denoted 200 and an "enzyme label" is denoted 300 for the bioanalytical studies. The probe oligonucleotide 100 here specifically reacts with a complementary analyte molecule 200 (this may be a target nucleic acid or control nucleic acid) and in this way immobilizes in an array-position-specific manner an enzyme label 300. Enzyme substrate 400 which is then added is converted into a product 500 by the catalytic action of the enzyme label.

The decrease/increase of substrate/product can be measured with the aid of the electrodes 2, 3 on the sensor element. By way of example, a detectable product 500 which may be mentioned here is the redox pair p-aminophenol/quinonimine:

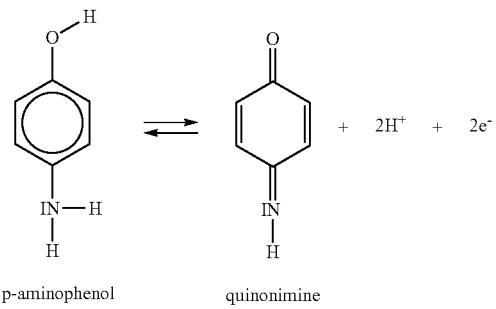

p-aminophenol      quinonimine

The corresponding redox process involves 2 electrons and 2 H$^+$ ions.

This system is employed, for example, in enzyme-coupled detection reactions. This involves using the enzyme "alkaline phosphatase" by way of a label or enhancer substance. Alkaline phosphatase is capable of cleaving p-aminophenyl phosphate to give p-aminophenol and phosphate:

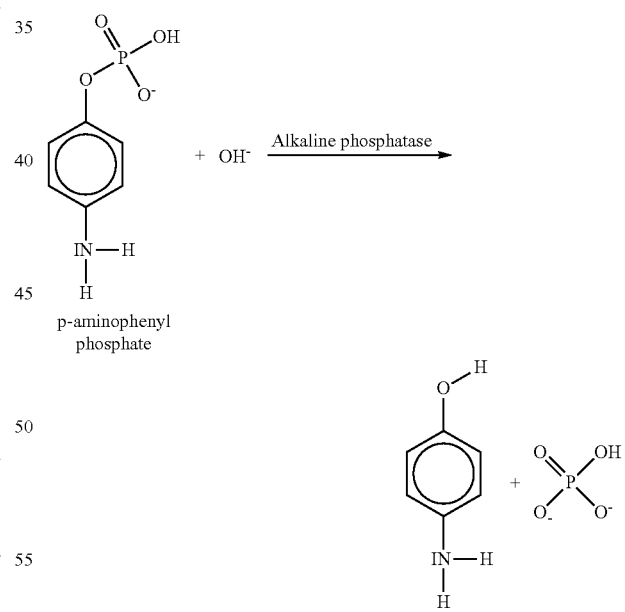

The p-aminophenol produced is oxidized on the electrode system or the redox pair p-aminophenol/quinonimine is cycled. The signal may then be measured off the electrodes as an increase in current (I) over time (t), with signal strength $S = dI/dt$.

Figure 2:
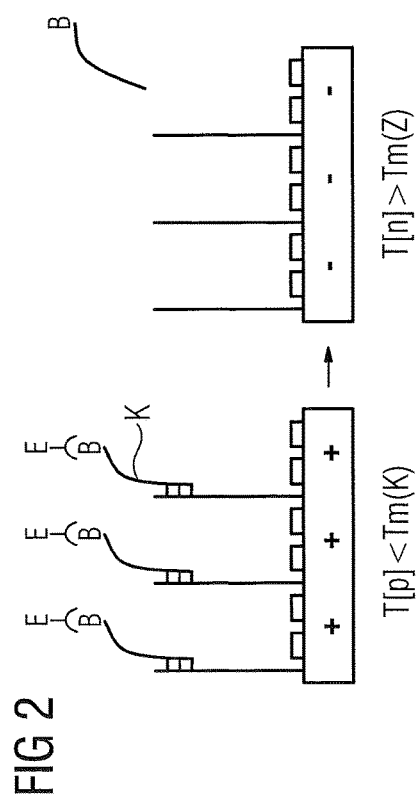
FIG. 2: is a diagram of a first embodiment of the invention.

FIG. 2 depicts a diagram of a first embodiment of the invention. A sensor element is charged with control nucleic acids (K) at a temperature T[p]<Tm(K), where Tm(K) is the melting temperature of the duplex of probe oligonucleotide and control nucleic acid under given solvent conditions. The concentration of the control nucleic acid is sufficiently high for enabling all free probe oligonucleotides to be saturated. At temperature T[p], the control nucleic acid molecules hybridize to any free probe oligonucleotides. The control nucleic acid is labeled with biotin (B). Streptavidin-conjugated enzyme (E) is then added which binds to biotin (B) and can convert a substrate (not shown), thereby enabling a signal (+) to be measured off the sensor element.

At temperature T[p], all probe oligonucleotides are saturated with control nucleic acid, and therefore a maximum signal is obtained as positive control signal.

The temperature is then increased to T[n]>Tm(K). The duplexes of probe oligonucleotide and control nucleic acid melt open, thereby releasing the control nucleic acids which may be rinsed away together with the enzyme. At temperature T[n], all probe oligonucleotides are now unsaturated again, and therefore no signal (−) or only a noise signal is measured and a minimum signal is obtained as negative control signal.

The values of the positive control signal and the negative control signal may be stored, for example, in a control device and utilized further as future reference values. In this way it is possible to carry out a specific calibration for the individual positions of a microarray, which involves calibrating each array position (each "spot") by the method depicted in FIG. 2. This may also be carried out for quality control of the microarray.

Figure 3:
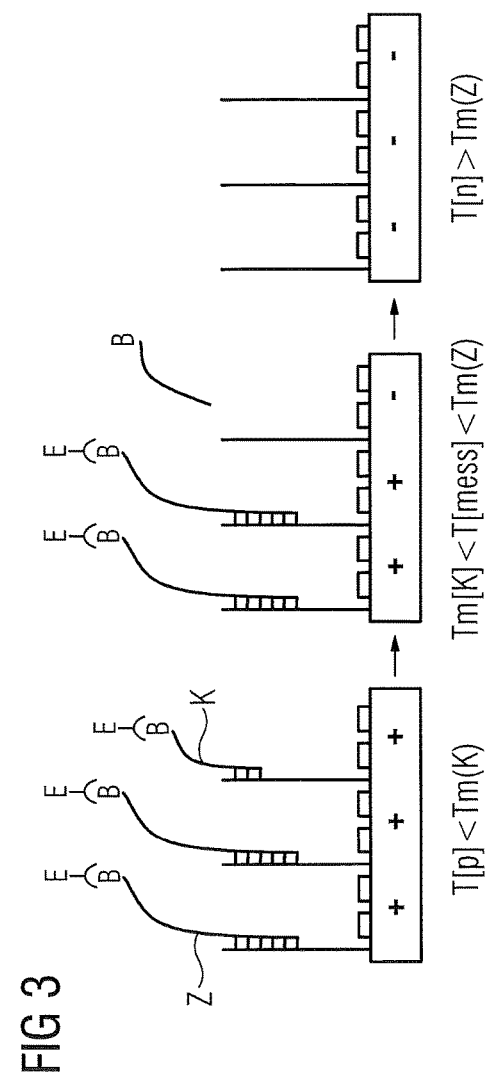
FIG. 3: is a diagram of another embodiment of the invention.

FIG. 3 depicts a diagram of another embodiment of the invention. A sensor element is charged with a sample which is suspected of containing the target nucleic acid (Z) for a corresponding probe oligonucleotide. Furthermore, control nucleic acid (K) is added to that. The temperature is T[p]<Tm(K), where Tm(K) is the melting temperature of the duplex of probe oligonucleotide and control nucleic acid under given solvent conditions (in addition Tm(K)<Tm[Z]). The concentration of the mixture of target nucleic acid and control nucleic acid is sufficiently high for enabling all free probe oligonucleotides to be saturated with target nucleic acid or control nucleic acid. At temperature T[p], the target and control nucleic acid molecules hybridize to any free probe oligonucleotides. The control nucleic acid is labeled with biotin (B). Streptavidin-conjugated enzyme (E) is then added, which binds to biotin (B) and can convert a substrate (not shown), thereby enabling a signal (+) to be measured off the sensor element.

At temperature T[p], all probe oligonucleotides are then saturated with target or control nucleic acid, and therefore a maximum signal is obtained as positive control signal.

The temperature T[mess] is then increased to Tm(K)<T[mess]<Tm(Z), where Tm(Z) is the melting temperature of the duplex of probe oligonucleotide and control nucleic acid under given solvent conditions. The duplexes of probe oligonucleotide and control nucleic acid melt open, thereby releasing the control nucleic acids which (together with the enzyme bound thereto) can be rinsed away. At temperature T[mess], only the probe oligonucleotides occupied with target nucleic acid still provide a signal (+) which is a measurement signal for the target nucleic acid.

The temperature is then increased to T[n]>Tm(Z). The duplexes or hybrids of probe oligonucleotide and target nucleic acid now also melt open, thereby releasing the target nucleic acids which (together with the enzyme) can be rinsed away. At temperature T[n], all probe oligonucleotides are now unsaturated again, and therefore no signal (−) or only a noise signal is measured and a minimum signal is obtained as negative control signal.

The signal strength of the target nucleic acid, S[Z], may then be expressed, for example, in relation to the positive control signal and negative control signal, for example according to the formula:

$$S[Z]=(S[\text{mess}]-S[n])/(S[p]-S[n]).$$

In this way, the sensor element may be simultaneously calibrated during each measurement, thus making possible a measurement with particularly high accuracy.

The sequence of the control nucleic acid, for example, is chosen so as to bind to the probe oligonucleotide over a shorter complementary sequence than the target nucleic acid. Alternatively, the control nucleic acid may also have a lower GC content or a combination of lower GC content and shorter complementary binding sequence than the target nucleic acid. This is depicted merely by way of diagrams in FIGS. 2 to 6. Only for reasons of clarity, the target nucleic acid is depicted with five binding base pairs and the control nucleic acid is depicted with two binding base pairs. The target nucleic acid binds preferably over a region of 15 or more, more preferably 30 or more, binding base pairs.

If the target nucleic acid binds to the probe oligonucleotide over a complementary region of approx. 20 to 25 bases, the complementary region of the control nucleic acid may be chosen, for example, with a length of from 6 to 12 bases. It is possible to choose a target nucleic acid which, in the complementary region, has a sequence which is partially identical to the target nucleic acid and therefore binds to some extent via the same nucleotides in the probe oligonucleotide as the target nucleic acid. It is also conceivable to use as control nucleic acid short oligomers with randomized sequences, for example randomized hexamers, randomized decamers or the like.

According to an alternative embodiment, the probe oligonucleotide has a region with a sequence which cannot hybridize to the target nucleic acid but only to the control nucleic acid. According to another embodiment, this region may be separated from the sequence binding the target nucleic acid by a spacer, making it even possible for target nucleic acid and control nucleic acid to bind simultaneously to the same probe oligonucleotide molecule. This is depicted, for example, in FIG. 4, where both the shorter control nucleic acid and the longer target nucleic acid can bind to a probe oligonucleotide at different regions of the probe oligonucleotide. Otherwise, the method of FIG. 4 is carried out according to the method of FIG. 3.

FIG. 5 depicts a diagram of another embodiment of the invention, in which a melting point curve of the target nucleic acid (Z) is determined. A sensor element is charged with a sample which is suspected of containing the target nucleic acid for a corresponding probe oligonucleotide. As in the method of FIG. 3, control nucleic acid (K) is also added to this. The temperature is T[p]<Tm(K), where Tm(K) is the melting temperature of the duplex of probe oligonucleotide and control nucleic acid under given solvent conditions. The concentration of the mixture of target nucleic acid and control nucleic acid is sufficiently high for enabling all free probe oligonucleotides to be saturated with target nucleic acid or control nucleic acid. At temperature T[p], the target and control nucleic acid molecules hybridize to any free probe oligonucleotides. The control nucleic acid is labeled with biotin (B). Streptavidin-conjugated enzyme (E) is then added, which binds to biotin (B) and can convert a substrate (not shown), thereby enabling a signal (+) to be measured off the sensor element.

At temperature T[p], all probe oligonucleotides are then saturated with target or control nucleic acid, and therefore a maximum signal is obtained as positive control signal.

The temperature is then increased step-by-step via T[mess 1] T[mess 2], etc., to T[p]<T[mess 1-n]<Tm(Z), and where Tm(Z) is the melting temperature of the duplex of probe oligonucleotide and target nucleic acid under given solvent conditions. The duplexes of probe oligonucleotide and control nucleic acid melt open first (as depicted in FIG. 5 at T[mess 1]), thereby releasing the control nucleic acids which (together with the enzyme bound thereto) can be rinsed away. At temperature T[mess 1], only the probe oligonucleotides occupied with target nucleic acid still provide a signal which is a measurement signal for the target nucleic acid. With the temperature increasing step by step, the duplexes of probe oligonucleotide and target nucleic acid then also start gradually to melt open (as depicted in FIG. 5 at T[mess 2]), thereby enabling a melting curve to be generated.

Finally, the temperature is then increased to T[n]>Tm(Z). The duplexes of probe oligonucleotide and target nucleic acid now melt open completely, thereby releasing all target nucleic acids which (together with the enzyme) can be rinsed away. At temperature T[n], all probe oligonucleotides are now unsaturated again, and therefore no signal (−) or only a noise signal is measured and a minimum signal is obtained as negative control signal.

Furthermore, an initial calibration measurement may be carried out with para-aminophenol (pAP), the primary substrate of the electrochemical reaction, in order to establish whether all electrodes react to the presence of this redox-reactive substance. This may be used to verify that all electrodes react to this redox-reactive product. Free para-aminophenol is then rinsed away, and a temperature-dependent sequence of measurements is started.

FIG. 6 depicts a diagram of another embodiment of the invention. The upper row summarizes the normal sequence of measurements, as described for FIG. 5:

Hybridization with target nucleic acid (Z) and control nucleic acid (K), measuring the positive control at T[p]<Tm (K), melting off the control nucleic acid, and generating the melting curve of the target nucleic acid at T[p]<T[mess 1-n]<Tm(Z), and recording the signal of the negative control at T[n]>Tm(Z). Probe oligonucleotides carrying a biotin are applied to other sensor elements of the sensor which are designed as separately displayed spots for temperature control (depicted in the lower row in FIG. 6). Here, the enzyme binds via the biotin-streptavidin complex to the probe oligonucleotides over the entire measured temperature range of T[p]<Tm(K), T[p]<T[mess 1-n]<Tm(Z), T[n]>Tm(Z), independently of the melting temperature of the DNA hybrids, and provides information on the dependency of the detection system (enzyme activity and electrochemical redox reaction) on the temperature. The signal strength on the measurement spots on which the target nucleic acid is measured may be corrected based on the temperature profile of the maximum signal.

It is also possible to provide for additional negative control spots which are coated with probe oligonucleotides having randomized sequences, which therefore cannot bind specifically the nucleic acid. This may compensate, inter alia, for unspecific binding effects and flow-dependent temperature effects. Finally, each sensor pair is calibrated for enzyme conversion (substrate turnover) in mole/(liter x s). Here too it is again possible to calculate a compensated signal from the signal strength for the measurement spot (carrying probe oligonucleotides which are specific for the target nucleic acid) and the negative control spot, for example by calculating difference or quotient.

It should be noted here that the examples are merely by way of illustration and example and that alterations and modifications are possible within the scope of protection of the claims. More specifically, the method of embodiments of the invention may be used in conjunction with other sensor elements and markers or labels, for example for optical, magnetic or gravimetric sensor elements.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method for calibrating all of the elements of a sensor, via which the sensor can record binding of a target nucleic acid(Z), the method comprising:

contacting all of the elements of a sensor comprising an array of a plurality of oligonucleotide probes immobilized to an electrochemical sensor via a gold surface, each of which oligonucleotide probes includes a first nucleotide sequence that hybridizes to the target nucleic acid at a temperature up to Tm(Z) and a second nucleotide sequence that hybridizes to the control nucleic acid at a temperature up to Tm(K), the first nucleotide sequence and the second nucleotide sequence having a different number of binding base pairs, the second nucleotide sequence having fewer nucleotides than the first nucleotide sequence or both of fewer nucleotides than the first nucleotide sequence and a lower percentage of G and C nucleotides than the first nucleotide sequence, with a mixture having a control nucleic acid (K) and the target nucleic acid(Z), a melting temperature of a complex of the control nucleic acid and the immobilized probe Tm(K) being lower than a melting temperature of a complex of the target nucleic acid and the immobilized probe Tm(Z), Tm(K) being the temperature below which the control nucleic acid (K) hybridizes with an associated immobilized probe oligonucleotide, and Tm(Z) being the temperature below which the target nucleic acid (Z) hybridizes with an associated immobilized probe oligonucleotide;

hybridizing the control nucleic acid (K) to the all of the associated probe oligonucleotides at a temperature T[p] <Tm(K), and recording an electrochemical positive control signal, T[p] being a temperature at which the electrochemical positive control signal is measured;

modifying stringency conditions at a measuring temperature T[mess] such that,

Tm(K)<T[mess]<Tm(Z), T[mess] is the temperature at which an electrochemical measurement signal is measured;

modifying the stringency conditions such that T[n]>Tm (Z); and recording an electrochemical negative control signal, T[n] is a temperature at which the electrochemical negative control signal is recorded.

2. The method as claimed in claim 1, wherein the stringency conditions are modified by increasing the temperature.

3. The method as claimed in claim 1, wherein an electrochemical measurement signal n is measured at a different temperature T[mess [[1-]]n], where Tm(K)<T[mess [[1-]]n]<Tm(Z).

4. The method as claimed in claim 1, wherein the target nucleic acid and the control nucleic acid are labeled with electrochemically detectable labels.

5. The method as claimed in claim 4, wherein at least one of the electrochemically detectable labels is an enzymatic label capable of converting a substrate into a product detectable by the electrochemical sensor element.

6. The method as claimed in claim 1, that further comprises contacting all of the sensor elements with an electrochemically detectable product in order to record a first calibration signal.

7. The method as claimed in claim 4, wherein additionally a temperature compensation signal is recorded from an additional element comprising the same electrochemically detectable label directly immobilized on an electrochemical sensor at each of the temperatures T[p], T[mess], T[mess n] and T[n], T[mess n] being the temperature at which an electrochemical measurement signal n is measured.

8. The method as claimed in claim 1, wherein the melting temperature Tm(K) of the complex of the control nucleic acid (K) and the immobilized probe is at least 5° C. lower than the melting temperature Tm(Z) of the complex of the target nucleic acid (Z) and the immobilized probe.

9. The method of claim 1, in which the first and second nucleotide sequences are different nucleotide sequences.

10. The method of claim 1, in which the second nucleotide sequence has a lower GC content than the first nucleotide sequence.

11. The method of claim 6, in which the electrochemically detectable product is a product of an enzyme reaction, said enzyme being bound to said control nucleic acid.

12. The method of claim 6, in which the first and second nucleotide sequences are different nucleotide sequences.

13. The method of claim 6, in which the second nucleotide sequence has a lower GC content than the first nucleotide sequence.

* * * * *